(12) United States Patent
Smith, III et al.

(10) Patent No.: US 6,455,570 B1
(45) Date of Patent: Sep. 24, 2002

(54) POLYPYRROLINONE BASED INHIBITORS OF MATRIX METALLOPROTEASES

(75) Inventors: Amos B. Smith, III, Merion, PA (US); Ralph F. Hirschmann, Blue Bell, PA (US); Thomas Nittoli, West Caldwell, NJ (US); Paul Sprengeler, El Granada, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/973,493

(22) Filed: Oct. 9, 2001

Related U.S. Application Data

(60) Provisional application No. 60/238,375, filed on Oct. 6, 2000.

(51) Int. Cl.$^7$ .................... A61K 31/40; C07D 207/24
(52) U.S. Cl. ........................... 514/422; 548/519
(58) Field of Search ............... 548/519; 514/422

(56) References Cited

U.S. PATENT DOCUMENTS 5,489,692 A * 2/1996 Hirschmann et al. ....... 548/519
5,514,814 A   5/1996 Hirschmann et al.
5,770,732 A * 6/1998 Hirschmann et al. ....... 544/141

OTHER PUBLICATIONS

Smith AB 3rd, Nittoli T, Sprengeler PA, Duann JJ, Liu RQ, Hirshmann RF. "Design, synthesis, and evaluation of a pyrrolinone– based matrix metalloprotease inhibitor". Nov. 30, 2000, Organic Letters, 2(24): 3809–12.*
Birkedal–Hansen, H., Curr. Opin. Cell Biol., 1995, 7:728.
Johnson, L.L., Dyer, R., Hupe, D.J., Curr. Opin. Chem. Biol., 1998, 2:466.
Johnson, W.H., et al., J. Enzyme Inhib., 1987 2:1.
Borkakoti, N., et al., Struct. Biol., 1994, 1(2):106–110.
Sudoh, M. et al., Pharm. Res., 1998, 15(5) 719–25.
R. Babine And S. Bender, Chem. Rev., 1997, 97:1359.
Whittaker, M. et al., Chem. Rev., 1999, 99:2735–76.
Smith, A. B., III, et al., Org. Lett., 2000, 2(24):2809–12.
Smith, A. B., III, et al., Bioorg. Med. Chem., 1999, 7:9–22.
Smith, A. B., III, et al., Tetrahedron Lett., 1997, 38(22):3809–3812.
Smith, A. B., III, et al., Tetrahedron Lett., 1993, 34(1):63–66.
Smith, A. B., III, et al., Biopolymers (Peptide Science), 1995, 37:29–53.
Smith, A. B., III, et al., J. Am. Chem. Soc., 1992, 114, 10672–64.
Smith, A. B., III, et al., J. Med. Chem., 1994, 37, 215–18.
Smith, A. B., III, et al., Bioorg. Med. Chem., 1996, 4(7):1021–24.
Smith, A. B., III, et al., J. Am. Chem. Soc., 1994, 116,9947.
Smith, A. B., III., et al., J. Am. Chem. Soc., 1998, 120, 12704.
Smith, A. B., III, et al., J. Am. Chem. Soc., 1999, 121:9286–98.
Smith, A. B., III, et al., J. Med. Chem., 1997, 40, 2440–44.
Smith, A. B., III, et al., J. Am. Chem. Soc., 1995, 117, 11113–23.
Hirschmann, R., et al., In New Perspectives in Drug Design: Dean, P.M., Jolles, G., Newton, C.G., Eds.; Academic: London, 1995, pp 1–14.
Smith, A. B., III, et al., Org Lett, 2000, 2(4):2037.
Smith, A. B., III et al. Org Lett 2000 2(4):2041.

* cited by examiner

Primary Examiner—Joseph K. McKane
Assistant Examiner—Sameena Ahmed
(74) Attorney, Agent, or Firm—Mathews, Collins, Shepherd & McKay, P.A.

(57) ABSTRACT

A compound of the formula

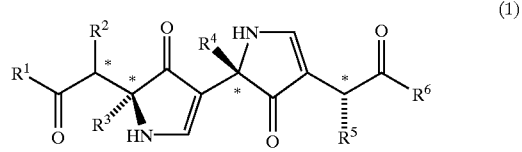

(1)

wherein: R1, R2, R3, R4, R5, R6 are as defined herein, useful for the inhibition of inhibition of matrix metalloproteases (MMPs)and for treating conditions mediated by elevated levels of MMPs such as osteoarthritis, rheumatoid arthritis, septic arthritis, periodontal disease, gingivitis, solid tumor growth and tumor invasion by secondary metastasis, corneal ulceration, dermal ulceration, epidermolysis bullosa, neural degeneration, multiple sclerosis and surgical wound healing.

9 Claims, 5 Drawing Sheets

POLYPYRROLINONE BASED INHIBITORS OF MATRIX METALLOPROTEASES

CROSS-REFERENCE TO PRIOR APPLICATIONS

This application claims the benefit of the following provisional application: U.S. Ser. No. 60/238,375 filed Oct. 6, 2000.

GOVERNMENT RIGHTS

This invention was made with Government support under Grant No. AI-42010 awarded by the National Institutes of Health through the National Institute of Allergy and Infectious Diseases. The government has certain rights in this invention.

SUMMARY OF THE INVENTION

Most tissues exist in a highly regulated dynamic equilibrium wherein new tissue is formed and existing tissue is degraded and eliminated. The degradation of the extracellular matrix (ECM), including connective tissue and basement membranes, is effected by the metalloproteinases which are released from connective tissue and invading inflammatory cells. There are at least four distinct groups of the more than 20 matrix metalloproteinases (MMP) which have been identified (Birkedal-Hansen, H. *J. Oral Pathol.* 1988 17:445; Birkedal-Hansen, H. *Curr. Opin. Cell Biol.* 1995 7:728; Emonard, H.; Grimaud, J. A. *Cell. Mol. Biol.* 1990 36:131; Murphy, G.; Docherty, A. J. P. *Am. J Respir. Cell Mol. Biol.* 1992 7:120; Baramova, E.; Foidart, J. *Cell Biol. Int.* 1995 19:239; Borkakoti, N. *Prog. Biophys. Mol. Biol.* 1998 70:73; Johnson, L. L., Dyer, R., Hupe, D. J. *Curr. Opin. Chem.Biol.* 1998 2:466; Shapiro, S. D.; Senior, R. M. *Am. J. Respir. Cell Mol. Biol.* 1999 20:1100): the collagenases (interstitial collagenase, MMP-1; PMN collagenase, MMP-8, collagenase-3, MMP- 13), the gelatinases (gelatinase A, MMP-2, 72 kDa-gelatinase, Type IV collagenase; gelatinase B, MMP-9, 92 kDa-gelatinase, Type IV collagenase) the stromelysins (proteoglycanase, MMP-3, stromelysin-1, transin; stromelysin-2, MMP-10; stromelysin 3, MMP-11) and the membrane type matrix metalloproteinases (MT-1, MMP-14; MT-2, MMP-15; MT-3, MMP-16 and MT-4, MMP-17). Excessive unregulated activity of these enzymes can result in undesirable tissue destruction and their activity is regulated at the transcription level, by controlled activation of the latent proenzyme and, after translation, by intracellular specific inhibitory factors such as TIMP ("Tissue Inhibitors of MetalloProteinase") or by more general proteinase inhibitors such as α2-macroglobulins.

Inhibitors of MMPs also have been found to inhibit the release of the pleiotropic proinflammatory cytokine, tumor necrosis factor alpha which has be associated with the pathogenesis of numerous inflammatory, autoimmune, and neoplastic diseases. The protease, TNFα-Converting Enzyme (TACE), catalyzes the release of TNFα from a membrane bound precursor protein.

The MMPs are a family of related proteolytic enzymes. They are zinc-binding metalloproteases linked by structural homology and by proteolytic activity against various components of the ECM while exhibiting divergent substrate specificity and activities. Calcium is generally required for maximum activity. They are distinguished from other metalloproteases by their susceptibility to activation of the zymogen by thiol-modifying reagents, mercurial compounds, N-ethylmaleimide and oxidized glutathione, by their inhibition by a group of endogenous substances known collectively as TIMPs, and by the presence of a consensus sequence in their propeptide forms. (H. Nagase, "Matrix Metalloproteinases," chapter 7, pp153–204 in *Zinc Metalloproteases in Health and Disease* "N. M. Hooper (ed.), Taylor and Francis, London (1996)).

Many pathological conditions are associated with the rapid unregulated breakdown of extracellular matrix tissue by MMPs. Some of these conditions include rheumatoid arthritis, osteoarthritis, septic arthritis, corneal, epidermal or gastric ulceration; periodontal disease, proteinuria, coronary thrombosis associated with atherosclerotic plaque rupture and bone disease. The process of tumor metastasis and angiogenesis also appears to be dependent on MMP activity. Since the cycle of tissue damage and response is associated with a worsening of the disease state, limiting MMP-induce tissue damage due to elevated levels of the proteinases with specific inhibitors of these proteases is a generally useful therapeutic approach to many of these debilitating diseases (for a general review see R C Wahl, et al. *Ann. Rep, Med. Chem.* 1990 25:175–184; Zask, A.; Levin, J. I.; Killar, L. M., Skotnicki, J. S. *Curr. Pharm. Des.* 1996, 2, 624).

It is an object of the present invention to provide novel selective, small molecule inhibitors of matrix metalloproteinases which can be used to modulate the progression of the underlying diseases and to treat diseases associated with excessive MMP-induced tissue damage.

BRIEF DESCRIPTION OF THE DRAWINGS

Specific embodiments of the invention have been chosen for the purpose of illustration and description but are not intended in any way to restrict the scope of the invention.

These embodiments are shown in the accompanying drawings wherein:

FIG. 4 depicts the conversion of the ester 18c into a hydroxamic acid 1a.

DETAILED DESCRIPTION OF THE INVENTION

Figure 1:
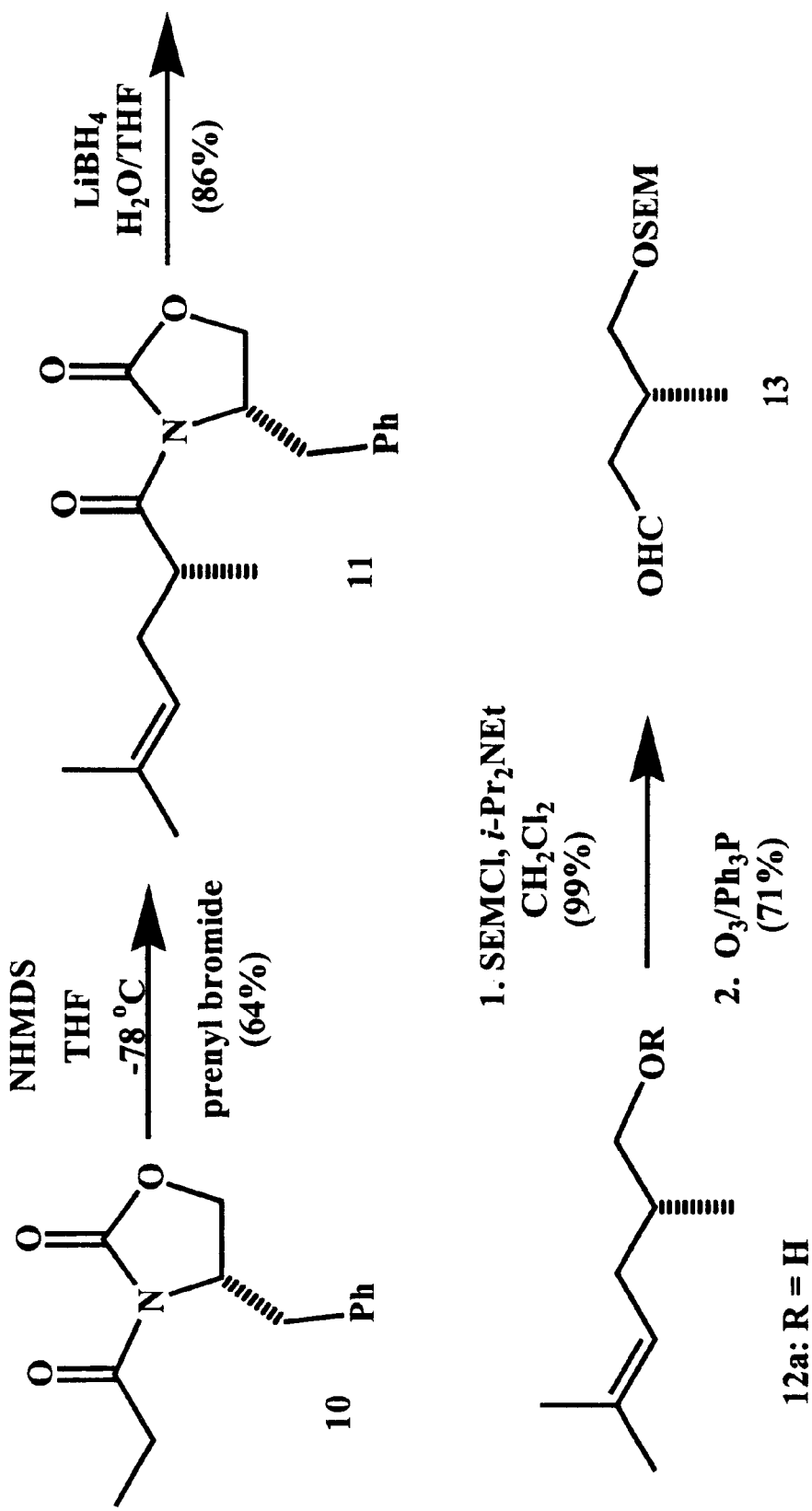
FIG. 1 depicts the preparation 2-(trimethylsilyl) ethoxymethyl protected aldehyde 13.

The invention encompasses novel polypyrrolidone compounds of formula 1 which are useful inhibitors of matrix metalloproteinases associated with inflammatory neoplastic and degenerative diseases and/or inhibitors of TNFα activity associated with inflammatory, autoimmune and neoplastic diseases.

Novel compounds of the present invention are of general formula 1:

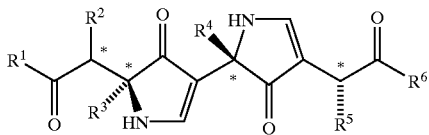

wherein:
R$^1$ is —NHOH or —OH;
R$^2$ is hydrogen, C$_{1-6}$ alkyl;
R$^3$ and R4 are selected independently from a group consisting of the side chains of naturally occurring α-amino acids, C$_{1-6}$ alkyl, (CH$_2$)$_n$Ar wherein the aryl group is optionally substituted with up to two groups independently selected from the group consisting of phenyl, hydroxy, C$_{1-4}$ alkoxy, phenoxy, —O(CH$_2$)$_m$OH, C$_{1-4}$ thioalkyl, halogens, nitro, cyano, C1$_{-4}$ alkylsulfonyl, and C$_{1-4}$ alkylsulfinyl wherein m is 1 or 2 and n is 0 to 3;
R$^5$ is hydrogen, C$_{1-6}$ alkyl;
R$^6$ is OR$^7$, NR$^7$R$^8$ wherein R$^7$ and R$^8$ taken independently are selected from a group consisting of hydrogen, C$_{1-4}$ alkyl, C$_{1-4}$ branched alkyl, alkyl aryl and benzyl; and,
a stereoisomer, enantiomer, diastereomer, hydrate or pharmaceutically acceptable salt thereof Another embodiment of the invention is a compound of formula 1 wherein:
R$^1$ is —NHOH or —OH
R$^2$ is H or CH$_3$;
R$^3$ is n-C$_{1-6}$ alkyl, s-C$_4$H$_9$, i-C$_4$H$_9$, (CH$_2$)$_n$Ar, (CH$_2$)$_n$-p-C$_6$H4OMe, (CH$_2$)$_n$-p-C$_6$H$_4$—C$_6$H$_5$ or (CH$_2$)$_n$-p-C$_6$H$_4$OC$_6$H$_5$ and n is 0 to 2;
R$^4$ is hydrogen, Me, i-C$_4$H$_9$ or n-C$_4$H$_9$;
R$^5$ is hydrogen, Me;
R$^6$ is OR$^7$ or NR$^7$R$^8$ wherein R$^7$ and R$^8$ are selected independently from the group consisting of hydrogen, Me, Et or CH$_2$Ph.

Yet another embodiment is a compound according to formula 1 wherein:
R$^1$ is —NHOH or —OH;
R$^2$ is H or CH$_3$;
R$^3$ and R$^4$ are selected independently from the group consisting of the side chains of naturally occurring α-amino acids;
R$^5$ is hydrogen, C$_{1-6}$ alkyl;
R$^6$ is OR$^7$ or NR$^7$R$^8$ wherein R$^7$ and R$^8$ are selected independently from the group consisting of hydrogen, Me, Et or CH$_2$Ph.

A further embodiment is a compound according to formula 1 wherein:
R$^1$ is —NHOH or —OH;
R$^2$ is H or CH$_3$;
R$^3$ and R$^4$ are selected independently from the group consisting of the side chains of naturally occurring hydrophobic α-amino acids;
R$^5$ is hydrogen, C$_{1-6}$ alkyl;
R$^6$is OR$^7$ or NR$^7$R$^8$ wherein R$^7$ and R$^8$ are selected independently from the group consisting of hydrogen, Me, Et or CH$_2$Ph.

An alternate embodiment is a compound according to formula 1 wherein:
R$^1$ is —NHOH
R$^2$ is H;
R$^3$ and R$^4$ are i-C$_3$H$_7$; i-C$_4$H$_9$, s-C$_4$H$_9$, CH$_2$C$_6$H$_5$, CH$_2$C$_6$H$_4$-p-OMe, (3-indolinyl)methyl;
R$_5$ is hydrogen, CH$_3$;
R$^6$ is OR$^7$; and,
R$^7$ is Me or Et;

Yet another embodiment is a method of inhibiting pathological changes mediated by elevated levels of matrix metalloproteases in mammals comprising administration to a mammal in need thereof a therapeutically effective amount of a matrix metalloprotease inhibiting compound according to formula 1.

Still another embodiment of the present invention is a method of treating an inflammatory disorder comprising administration to a mammal in need thereof a therapeutically effective amount of a matrix metalloprotease inhibiting compound according to formula 1.

Yet another embodiment is a method for treating a condition mediated by elevated MMP levels with a compound according to formula 1 wherein the condition treated is osteoarthritis, rheumatoid arthritis, septic arthritis, periodontal disease, gingivitis, solid tumor growth and tumor invasion by secondary metastasis, corneal ulceration, dermal ulceration, epidermolysis bullosa, neural degeneration, multiple sclerosis and surgical wound healing..

Another embodiment of the current invention is a pharmaceutical composition comprising a pharmaceutical carrier and a therapeutically effective amount of a matrix metalloprotease inhibiting compound according to formula 1.

The phrase "a" or "an" entity as used herein refers to one or more of that entity; for example, a compound refers to one or more compounds or at least one compound. As such, the terms "a" (or "an"), "one or more", and "at least one" can be used interchangeably herein.

The terms "comprising", "including" and "having" are used interchangeably. Furthermore, a compound "selected from the group consisting of" refers to one or more of the compounds in the list that follows, including mixtures (i.e., combinations) of two or more of the compounds.

The compounds of this invention may contain one or more asymmetric centers and may thus give rise to optical isomers and diastereomers. Carbons marked with an asterisk in formula 1 are asymmetric or can be asymmetric when R$^2$ and/or R$^5$ substituent is other than hydrogen. Furthermore, the substituents R$^2$–R$^6$ can contain additional asymmetric carbon atoms. The present invention includes all such optical isomers and diastereomers; as well as the racemic and resolved, enantiomerically pure R and S stereoisomers; as well as other mixtures of the R and S stereoisomers and pharmaceutically acceptable salts thereof. It is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

For the purpose of the present invention, the carbon content of various hydrocarbon containing moieties is indicated by a prefix designating the minimum and maximum number of carbon atoms in the moiety, i.e., the prefix $C_{i-j}$ defines the number of carbon atoms present from the integer "i" to the integer "j", inclusive.

As used herein, the term "alkyl" refers to a straight or branched chain alkyl moiety having from one to six carbon atoms, including for example, methyl, ethyl, propyl, iso-propyl, butyl, tert-butyl, pentyl, hexyl and the like.

As used herein, the term "alkoxy" refers to a straight chain or branched chain alkoxy group containing a maximum of six carbon atoms, such as methoxy, ethoxy, propoxy, iso-propoxy, butoxy, tert-butoxy and the like.

As used herein, the term "aryl" means an optionally substituted phenyl or naphthyl group with the substituent(s) being selected, for example, from halogen, trifluoromethyl, $C_{1-6}$ alkyl, $C_{1-6}$ alkoxy, phenyl and the like.

The term "aralkyl" as used herein refers to a optionally substituted alkylenephenyl group, wherein alkyl is lower alkyl and preferably from 1 to 3 carbon atoms, and aryl is as previously defined.

As used herein, the term "halogen" means bromine, chlorine, fluorine, and iodine.

As used herein, the term "naturally occurring amino acids" means the L-isomers of the naturally occurring amino acids. The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, y-carboxyglutamic acid, arginine, ornithine and lysine.

As used here, the term "side chain of an α-amino acid" refers to the substituents on the alpha carbon of the natural amino acids and include: hydrogen, methyl, i-propyl, i-bu, s-bu, —$CH_2OH$, —$CH(OH)CH_3$, —$CH_2SH$, —$CH_2CH_2SMe$, —$(CH_2)_pCOR$ wherein R is —OH or —$NH_2$ and p is 1 or 2, —$(CH2)_q$—$NH_2$ where q is 3 or 4, —$(CH_2)_3$—$NHC(=NH)NH_2$, —$CH_2C_6H_5$, —$CH_2$-p-$C_6H_4$—OH, (3-indolinyl)methylene, (4-imidazolyl) methylene.

As used herein, the term "hydrophobic amino acid" means any amino acid having an uncharged, nonpolar side chain that is relatively insoluble in water. Examples of naturally occurring hydrophobic amino acids are alanine, leucine, isoleucine, valine, phenylalanine, tryptophan, tyrosine and methionine.

Those skilled in the art will recognize that certain reactions are best carried out when other potentially reactive functionality on the molecule is masked or protected, thus avoiding undesirable side reactions and/or increasing the yield of the reaction. The terms "protected amino" and "protected carboxy" mean amino and carboxy groups which are protected in a manner familiar to those skilled in the art. Examples of these protecting group moieties may be found in T. W. Greene, P. G. M. Wuts "Protective Groups in Organic Synthesis", 2nd Edition, 1991, Wiley & Sons, New York. Reactive side chain functionalities on amino acid starting materials are preferably protected. The need and choice of protecting groups for a particular reaction is known to those skilled in the art and depends on the nature of the functional group to be protected (hydroxy, amino, carboxy, etc.), the structure and stability of the molecule of which the substituent is part and the reaction conditions. For example, an amino group can be protected by a benzyloxycarbonyl, tert-butoxycarbonyl, acetyl or like groups, or in the form of a phthalimido or like group.

Pharmaceutically acceptable salts can be formed from organic and inorganic acids, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, naphthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains an acidic moiety.

The following abbreviations have been used in this application:

| | |
|---|---|
| Bn | benzyl |
| cbz | benzyloxycarbonyl |
| CI | chemical ionization |
| EDCl | 1-ethyl-3(3'-dimethylaminopropyl)carbodiimide hydrochloride |
| ESI | electrospray ionization |
| HOBt | 1-hydroxybenzotriazole hydrate |
| KHMDS | potassium hexamethyldisilazane |
| MMP | Matrix Metalloprotease |
| SEM | 2-(trimethylsilyl)ethoxymethyl |
| SEMCl | 2-(trimethylsilyl)ethoxymethyl chloride |
| TFA | trifluoroacetic acid |
| THF | tetrahydrofuran |
| TIMP | Tissue Inhibitors of Metalloproteinase |
| Ts | p-toluenesulfonyl |

The role of the MMPs in a variety of serious and debilitating diseases has prompted attempts to identify potent and selective inhibitors of individual members of this class of proteases. Proteases have been excellent model systems for rational drug design studies and these efforts have provided numerous approaches which have been adapted to these enzymes. Naturally occurring polypeptides which are substrates or inhibitors of this class of proteases provide a natural starting point for chemical design and modification. The 2.2 Å resolution X-ray structure of potent peptidyl MMP inhibitor Ro-3 1-4724 (Johnson, W. H., et al. *J. Enzyme Inhib.* 1987 2:1), (3) co-crystallized with MMP-1 (Borkakoti, N., et al. *Struct. Biol.* 1994 1:106) provides useful insight from which non-peptide analogs can be envisioned. The well-established difficulties associated with the use and administration of labile peptides or large polypeptides as therapeutic agents, especially for long term treatment of chronic diseases, have made the identification of stable, easily administered peptide mimics highly desirable. Some of these classes of compounds now include, thiols (4) phosphorus (phosphonamides, phosphonates and phosphinates) (5) hydroxamates (6) and carboxylates (7) peptide derivatives. (R. C. Wahl and R. P. Dunlap, *Biochemistry and Inhibition of Collagenase and Stromelysin, Ann. Rep. Med. Chem.* (1990) 25:177–184; J. B. Summers and S. K. Davidson, *Matrix Metalloproteinases and Cancer, Ann. Rep. Med. Chem.* (1998) 33:131–140; R. Babine and S. Bender, *Chem. Rev.* (1997) 97:1359).

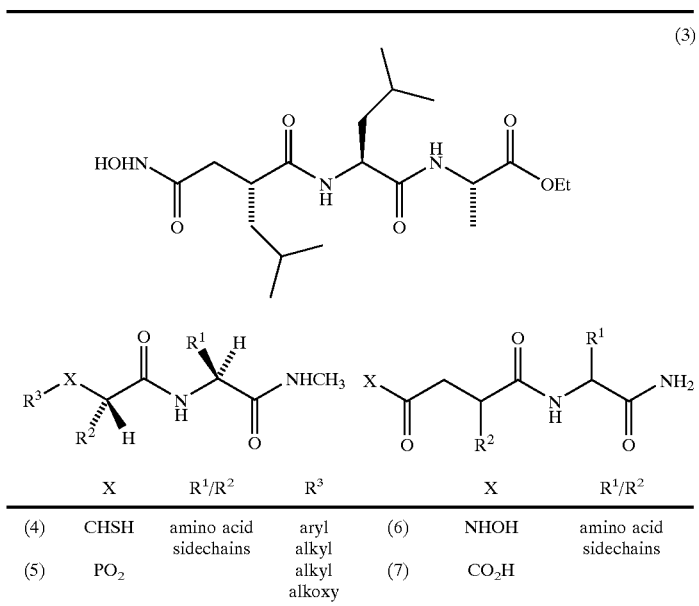

| | X | R¹/R² | R³ |
|---|---|---|---|
| (4) | CHSH | amino acid sidechains | aryl alkyl |
| (5) | PO₂ | | alkyl alkoxy |
| (6) | NHOH | amino acid sidechains | |
| (7) | CO₂H | | |

Despite the continuing efforts to identify specific and potent inhibitors of these potentially pathological mediators, there remains a need to identify MMP inhibitors, particularly low molecular weight inhibitors, with sufficient selectivity, potency and bioavailability to be useful clinical candidates. Peptidomimetics, non-peptides that mimic the structure of endogenous peptides, are stable to physiologic conditions and are bioavailable after oral administration. Although a variety of scaffolds have been identified which mimic secondary conformations of proteins and polypeptides, the enormous variety of conformations found in nature affords a continuing need to identify useful templates to mimic polypeptides.

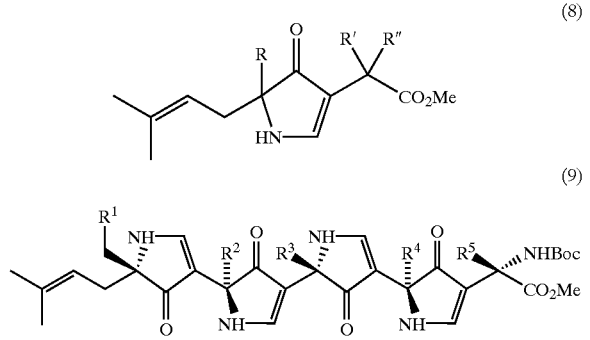

The 3,5,5-trisubstituted pyrrolin-4-one ring system, (8) has proven to be a versatile template for the design of peptidomimetics and polypyrrolinones (9) have been shown to be effective surrogates for polypeptides. Depending on their structure, polypyrrolinones, which are stable to both strong acid and proteases, can adopt diverse conformations including those analogous to β-strands (Smith, A. B., m et al., *J. Am. Chem. Soc.* 1992, 114, 10672; Smith, A. B., III et al., *J. Am. Chem. Soc.* 1994, 116, 9947), β-turns and helices (Smith, A. B., III et al., *Bioorg. Med. Chem.* 1999, 9). The β-strand structural motif was successfully utilized in the design and synthesis of several potent, bioavailable inhibitors of the HIV-1 aspartic acid protease which exhibited improved membrane transport properties relative to their peptidal counterparts. (Smith, A. B., III et al., *J. Med. Chem.* 1994, 37, 215; Smith, A. B., III, et al., *J. Am. Chem. Soc.* 1995, 117, 11113; Smith, A. B., III et al., *J. Med. Chem.* 1997, 40, 2440; Thompson, W. J., et al., *J. Med. Chem.* 1992, 35, 1685.) The improved transport was attributed to the presence of intramolecular hydrogen bonds between adjacent pyrrolinone rings (NH and CO), which led to a reduction in desolvation energy upon membrane transport (Hirschmann, R., et al. *In New Perspectives in Drug Design*; Dean, P. M., Jolles, G., Newton, C. G., Eds.; Academic: London, 1995; pp 1–14.). A bis-pyrrolinone was successfully used in the construction of a pyrrolinone-peptide hybrid ligand, which bound the Class II MHC protein HLA-DR1 in an extended β-strand-like conformation with similar potency to the native peptide. (Smith, A. B., III, et al. *J. Am. Chem. Soc.* 1998, 120, 12704; Smith, A. B., III; et al. *J. Am. Chem. Soc.* 1999, 121, 9286.) All references cited in this application are hereby incorporated into this application in their entirety.

The 3,5-linked (nitrogen displaced) pyrrolinone scaffold directly substitutes on a per residue basis for R-amino acids (except proline and glycine). (Smith, A. B. III, et al. *Biopolymers (Peptide Science)* 1995 37:29) Importantly, this structural motif derived from the D-amino acids maintains both the spacial orientation of the amino acid side chains and the capacity to form intermolecular hydrogen bonds with the receptor or enzyme. The advantage of nonpeptidyl peptidomimetics, in general, is their ability to resist degradation by proteases and to possess additional favorable pharmacokinetic properties as a result of reduced salvation.

Compounds of the present invention are available from a protocol exploiting the intramolecular cyclization of a met-alloenamine derived from an α-amino acid derivative. Those skilled in the art will recognize that the nature and order of the synthetic steps presented may be varied for the purpose of optimizing the formation of the compounds of the invention.

The synthesis of aldehyde 13 (FIG. 1) began with Evans alkylation of (S)-propionyloxazolidinone (+)-10 with prenyl bromide to furnish the oxazolidinone (+)-11 in 64% yield (>98% ee). Reduction with lithium borohydride in wet THF (Penning; T. D. et al. *Synth. Comm.* 1990 20:307) followed by protection of the hydroxyl with 2-(trimethylsilyl) ethoxymethyl chloride (SEM-Cl) led to the SEM ether, which was subjected to ozonolysis to furnish aldehyde (+)-13; the overall yield from (+)-10 was 39%.

Figure 2:
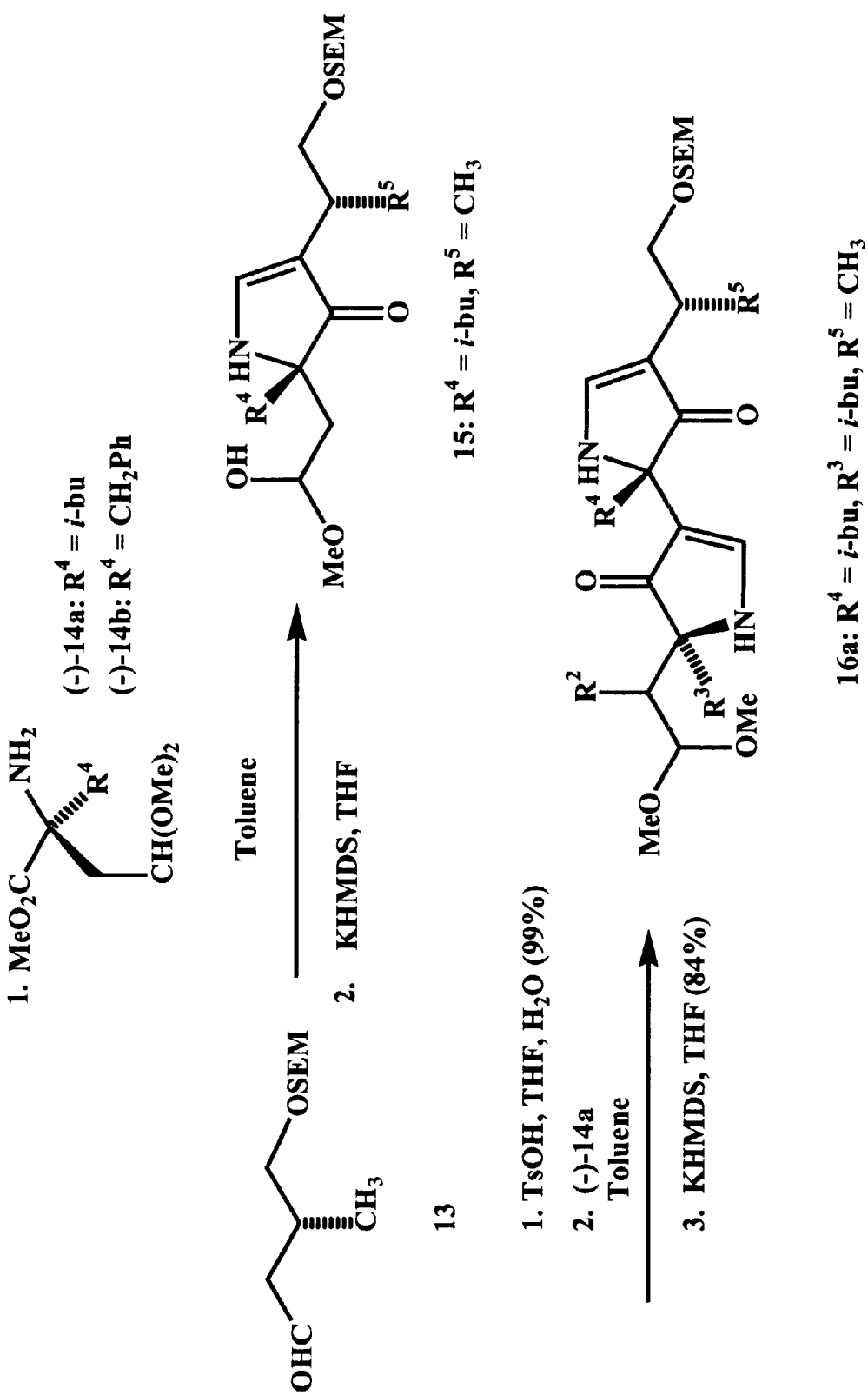
FIG. 2 depicts the intramolecular cyclization of a metalloenamine to prepare the bis-pyrrolidone 16.
Figure 3:
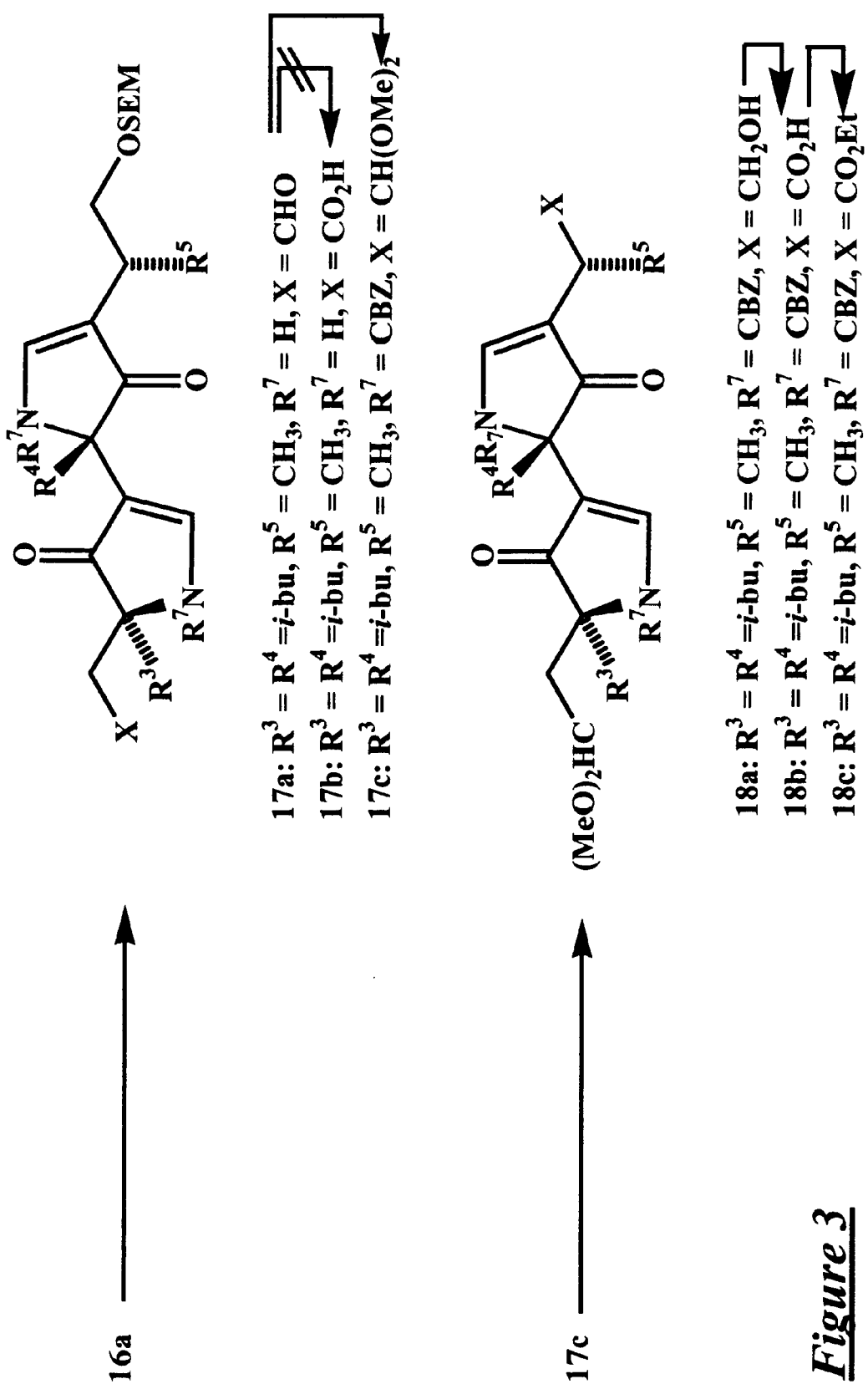
FIG. 3 depicts the functional group manipulation required to convert the bis-pyrrolinone to the ester 18c.
Figure 4:
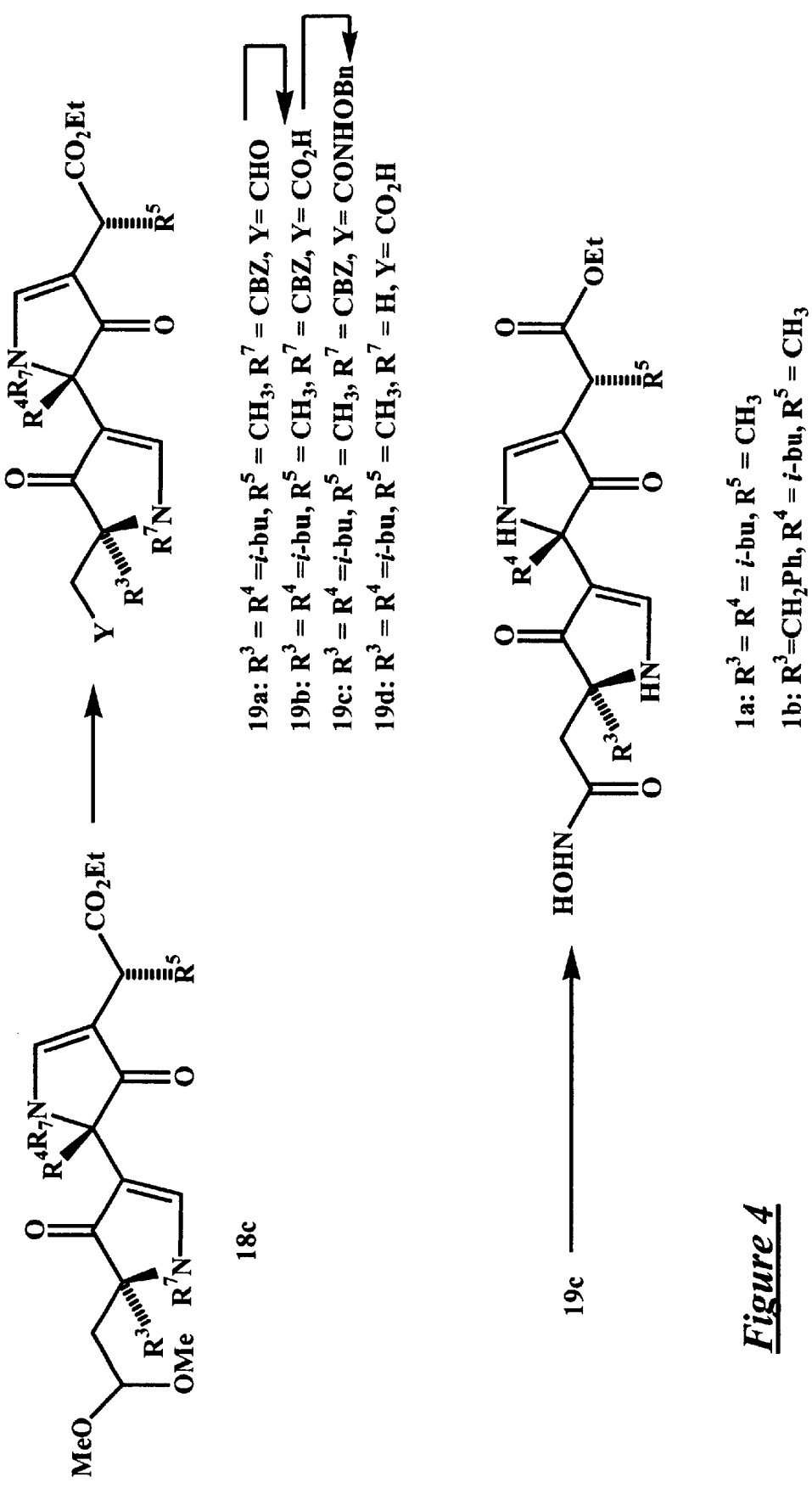

To construct monopyrrolinone (+)-15, amino ester (−)-14a was condensed with aldehyde (+)-13 (FIG. 2); dehydration and subsequent base-promoted pyrrolinone ring formation with KHMDS furnished (+)-15 in 93% yield (two steps). Hydrolysis of the dimethylacetal with TsOH at 40° C. led to the corresponding aldehyde in nearly quantitative yield. A second pyrrolinone ring was constructed using amino ester (−)-14a which led to bis-pyrrolinone (−)-16a. The efficiency of our iterative pyrrolinone construction protocol was clearly demonstrated by the 77% overall yield of (−)-16a from (+)-13. Hydrolysis of the dimethylacetal in (−)-16a was next achieved with 1 N HCl at 40° C. Unfortunately, oxidation of the derived aldehyde to the corresponding carboxylic acid by under a variety of different conditions (e.g., Jones, sodium chlorite, PCC, etc.) proceeded only in low yield. Careful examination of the product mixture revealed that the pyrrolinone rings were not stable to the oxidation conditions. To circumvent this problem, (−)-16a was protected as the bis-Cbz derivative (+)-17c (FIG. 3); although this operation led to a less reactive pyrrolinone ring, the acetal proved resilient to hydrolysis. The problem was solved by first removing the SEM group. Treatment of (+)-17c with TsOH and methanol at 40° C. furnished alcohol (+)-18a. A two-step oxidation with Dess-Martin periodinane (Dess, D. B. and Martin, J. C. *J. Org. Chem.* 1983 48:4155; Dess, D. B. and Martin, J. C. *J. Am. Chem. Soc.* 1991 113:7277; Ireland and R. E.; Liu, L. *J. Org. Chem.* 1993 58:2899) and then with sodium chlorite produced the acid 18b in 81% yield. Esterification followed by removal of the acetal (TsOH in wet THF at 40° C.) furnished the intermediate bis-pyrrolinone aldehyde; immediate oxidation with sodium chlorite led to (+)-18c. Completion of the synthesis was achieved via coupling (+)-19b with O-benzyl hydroxylamine (EDCI and HOBt), followed by hydrogenolysis with Pd/BaSO$_4$ (Nikam, S. S. *Tetrahedron Lett.* 1995 36:197–200). The overall yield of (−)1a for the two steps was 51%. The corresponding carboxylic acid 19d was prepared by hydrogenolysis of 19b.

Figure 5:
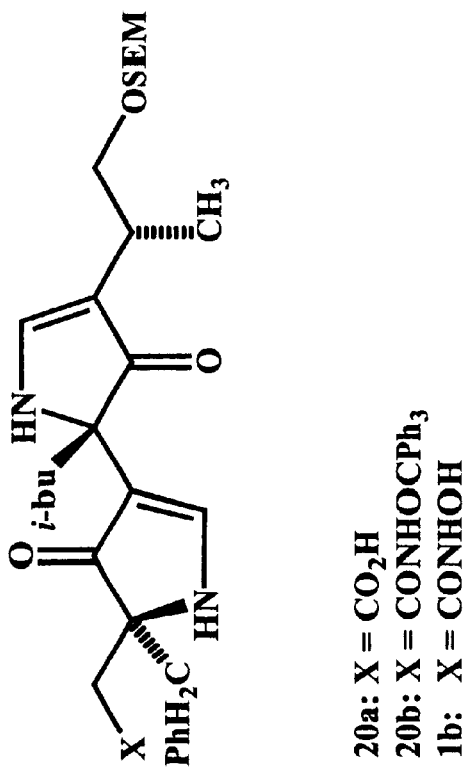
FIG. 5 depicts an alternate protection strategy utilizing and alloc protecting group in place of the CBZ group and the use of 0-trityl hydroxylamine to prepare the hydroxamic acid 1b.
Figure 5:
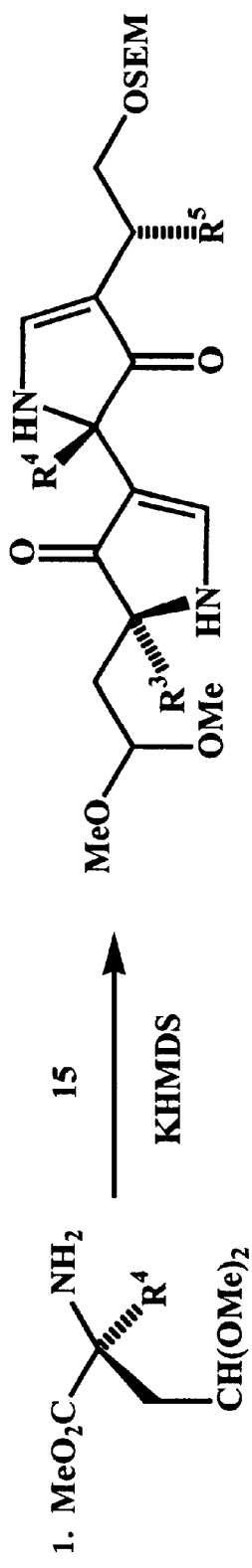
Figure 5:
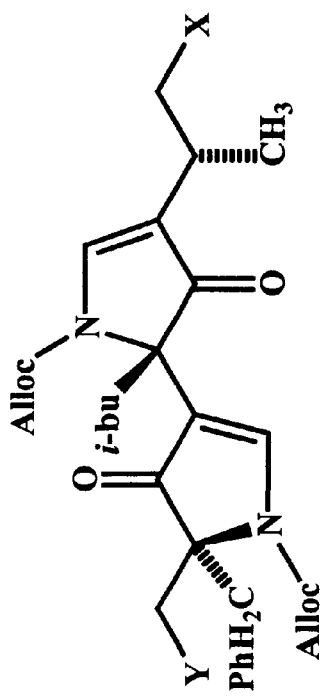

Those skilled in the art will appreciate that a variety of protecting groups and reagents can be employed. The hydroxamic acid 1b was prepared by a similar scheme (FIG. 5). The base catalyzed intramolecular cyclization was carried out with 14b which yielded the bis-pyrrolidone 16b. In this case the allyloxycarbonyl (Alloc) protecting group was used in place of the cbz group and 16b was protected as the bis-alloc derivative 19a which was converted to 19b. The alloc protecting group was removed with tetrakis-triphenylphosphine palladium(0) and dimedone. In this case the hydroxamic acid was introduced as the O-trityl derivative 20b which was deprotected with TFA to yield 1b.

Compounds of the present invention were assayed for metalloprotease activity by a published procedure (see, for example, J. Duan, WO/0059285). The bis-pyrrolinone (−)-1a exhibited inhibitory activity against gelatinase (MMP-2), matrilysin (MMP-7), and the membrane type 2 matrix metalloprotease (MMP-15) with K$_i$ values of 2.9, 6.4 and 6.8 μM, respectively. The bis-pyrrolinone carboxylic acid (−)-19d, on the other hand, failed to inhibit the ten proteases assayed, a result presumably of the shorter overall chain length compared to (−)-1a and/or the known reduced affinity of the carboxylate for zinc(II) compared to the hydroxamate functionality. (Whittaker, M. et al. *Chem. Rev.* 1999 99:2735; Borkakoti, N. et al. *Struct. Biol.* 1994 1:106)

Compounds of this invention may be administered neat or with a pharmaceutical carrier to a patient in need thereof. The pharmaceutical carrier may be solid or liquid.

Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such a solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferable sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

The compounds of this invention may be administered rectally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may also be administered transdermally through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels, and occlusive devices. The creams and ointments may be viscous liquid or semi-solid emulsions of either the oil in water or water in oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The dosage to be used in the treatment of a specific patient suffering a MMP dependent condition must be subjectively determined by the attending physician. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy. Treatment will generally be initiated with small dosages less than the optimum dose of the compound. Thereafter the dosage is increased until the optimum effect under the circumstances is reached. Precise dosages for oral, parenteral, nasal, or intrabronchial administration will be determined by the administering physician based on experience with the individual subject treated and standard medical principles.

GENERAL EXPERIMENTAL PROCEDURES

All reactions were carried out in oven-dried or flame-dried glassware under an argon atmosphere, unless otherwise noted. All solvents were reagent or high performance liquid chromatography grade. Tetrahydrofuran (THF) was freshly distilled from sodium/benzophenone under argon prior to use unless otherwise noted. Triethylamine and diisopropylethylamine were distilled from calcium hydride and stored over potassium hydroxide. Anhydrous dimethylformamide was purchased from Aldrich and used without purification. n-Butyllithium was purchased from Aldrich and standardized by titration with sec-butyl alcohol. All reactions were magnetically stirred and monitored by thin layer chromatography using 0.25 mm E. Merck pre-coated silica gel plates. Flash column chromatography was performed with the indicated solvents using silica gel-60 (particle size 0.040–0.062 mm) supplied by E. Merck. Yields refer to chromatographically and spectroscopically pure compounds, unless otherwise stated. The IR and NMR spectra were obtained for $CHCl_3$ and $CDCl_3$ solutions respectively unless otherwise noted. Infrared spectra were recorded with a Perkin-Elmer 1600 series FTIR spectrometer. Proton and carbon-13 NMR spectra were recorded on a Bruker AM-500 spectrometer and obtained at 305 K. Chemical shifts are reported relative to chloroform ($\delta 7.26$ for proton and $\delta 77.0$ for carbon-13). Optical rotations were obtained with a Perkin-Elmer model 341 polarimeter in the solvent indicated. High-resolution mass spectra were obtained at the University of Pennsylvania Mass Spectrometry Service Center on a Micromass (UK) AutoSpec spectrometer in electrospray or chemical ionization mode.

Example 1

Oxazolidinone (+)-11

To a solution of (S)-propionyl-oxazolidinone (10; 9.34 mmol) in THF (125 mL) at −78° C. was added 1.0 M NaHMDS in THF (41 mL, 41 mmol) over 1 h. The resulting solution was stirred for 15 min and then freshly distilled prenyl bromide (11.83 mL, 103 mmol) was added dropwise via syringe over 30 min. The clear yellow solution was stirred for 15 min at −78° C. and then warmed to 0° C. and stirred 45 min, where upon the solute became cloudy. The solution was then poured into 10% aqueous NaHSO4 (100 mL). The resulting biphasic mixture was extracted with EtOAc (2×100 mL) and the organic phase washed with saturated $NaHCO_3$ and brine (100 mL each), dried over $MgSO_4$ and concentrated in vacuo. The resulting yellow oil was purified by flash chromatography using ethyl acetate-hexanes (1:5) as the eluant to afford the alkylated oxazolidinone (6.6 g, 64% yield, >98% ee) as a clear colorless oil: $[\alpha]^{23}_D +40.9°$ (c 1.70, $CHCl_3$); IR (neat, film) 3380(w), 2973(s), 2917(s), 1770(s), 1694(s), 1289(s), 1212(s), 1100 (s), 1055(s), 1016(s) cm$^{-1}$; $^1$H NMR (500 MHz, $CDCl_3$) 07.28 (m, 5H), 5.19 (t, J=7.4 Hz, 1H),4.70 (m, 1H), 4.17 (m, 2H), 3.82 (sx, J=6.7 Hz, 1H), 3.25 (dd, J=3.3 Hz, 1H), 2.74 (dd, J=9.3 Hz, 1H), 2.47 (m, 1H), 2.21 (m; 1H), 1.72 (s, 3H), 1.66 (s, 3H), 1.18 (d, J=7.1 Hz, 3H); $^{13}$C NMR (125 MHz, $CDCl_3$) $\delta 176.88$, 152.99, 135.32, 133.77, 129.30, 128.80, 127.18, 121.04, 65.82, 55.10, 37.83, 37.79, 32.28, 25.70, 17.76, 16.32; high resolution mass spectrum (CI, $CH_4$) m/z 302.1746 [(M+H)]$^+$, calcd. for $C_{18}H_{24}NO_3$ 302.1756.

Example 2

Alcohol (+)-12a

To a solution of (+)-11 (13.9 g, 46 mmol) in $Et_2O$ (700 mL) at 0° C. was added $H_2O$ (2.65 g, 147 mmol) and 2.0 M $LiBH_4$ in THF (25 mL, 50 mmol) dropwise over 30 min. The resulting solution was stirred for 1 h and then warmed to room temperature. The reaction was quenched with saturated $NaHCO_3$ (200 mL). The resulting biphasic mixture was extracted with $Et_2O$ (3×125 mL), dried over $NaSO_4$, and concentrated in vacuo. The resulting yellow oil was purified by flash chromatography using $Et_2O$-hexanes (1:1) as the eluant to afford 12 (5.1 g, 86% yield) as a volatile clear colorless oil: $[\alpha]^{23}_D +4.3°$ (c 1.40, $CH_2Cl_2$); IR ($CHCl_3$) 3626(m), 3450(b), 3009(s), 2965(s), 2929(s), 2877(s), 1672 (w), 1377(s), 1028(s) cm$^{-1}$; $^1$H NMR (500 MHz, $CDCl_3$) $\delta 5.16$ (m, 1H), 3.52 (m, J=6.0 Hz, 1H), 3.44 (dd, J=6.3, 6.0 Hz, 1H), 2.07 (m, 1H), 1.88 (m, 1H), 1.71 (s, 3H), 1.69 (m, 1H), 1.62 (s, 3H), 1.37 (s, 1H). 0.92 (d, J=6.7 Hz, 3H); $^{13}$C NMR (125 MHz, $CDCl_3$) $\delta 132.47$, 122.56, 67.96. 36.47, 31.80, 25.70, 17.66, 16.48; high resolution mass spectrum (CI, $CH_4$) m/z 128.1201 (M)$^+$, calcd. for $C_8H_{16}O$ 128.1201.

Example 3

SEM Ether 12b

To a solution of (+)-12a (4.81 g, 38 mmol) in dichloromethane (18 mL) at 0° C. was added (i-Pr)$_2$NEt (33.10 mL, 190 mmol) dropwise over 15 min. To the resulting solution was added SEM-Cl (20.18 mL, 114 mmol) dropwise over 15 min. and the resulting solution was stirred for 2 h. The solution was then poured into 10% aqueous $NaHSO_4$ (100 mL). he resulting biphasic mixture was extracted with $Et_2O$ (3×100 mL), dried over $MgSO_4$ and concentrated in vacuo. The resulting orange oil was purified by flash chromatography using ethyl acetate-hexanes (1:5) as the eluant to afford the corresponding prenyl SEM ether (9.81 g, 99% yield) as a clear colorless oil: $[\alpha]^{23}_D -1.9°$ (c 2.59, $CHCl_3$); IR (neat film) 2953(s), 2921(s), 1248(s), 1109(s), 1058(s), 1038(s), 859(s), 835(s) cm$^{-1}$; $^1$H NMR (500 MHz, $CDCl_3$) $\delta 5.12$ (m, 1H), 4.65 (s, 2H), 3.61 (m, 2H), 3.40 (dd, J=3.6, 6.0 Hz, 1H), 3.30 (m, J=6.7 Hz, 1H), 2.07 (m, 1H), 1.85 (m, 1H), 1.74 (sx, J=6.7 Hz, 1H), 1.69 (s, 3H), 1.59 (s, 3H), 0.93 (m, 2H), 0.91 (d, J=6.7 Hz, 3H), 0.01 (s, 9H); $^{13}$C NMR (125 MHz, $CDCl_3$) $\delta 132.38$, 122.56, 94.94, 72.86, 64.82, 34.27, 31.98, 25.76, 18.11, 17.74, 16.96, −1.45; high resolution mass spectrum (CI, $NH_3$) m/z 276.2360 [(M+$NH_4$)]$^+$, calcd. for $C_{14}H_{30}O_2Si.NH_4$ 276.2359. Anal. Calcd. for $C_{14}H_{30}O_2Si$: C, 65.06; H,11.70. Found: C, 65.26; H,11.95.

Example 4

Aldehyde (+)-13

Ozone was bubbled through a solution of (−)-prenyl SEM ether 12b (6.6 g, 26 mmol) in dichloromethane (200 mL) at −78° C. until a pale blue color persisted. At −78° C., Ph$_3$P (6.69 g, 26 mmol) was then added and the reaction mixture allowed to stir and warm to room temperature overnight. The resulting clear oil was purified by flash chromatography using EtOAc-hexanes (1:5 then 3:10) as the eluant to afford the aldehyde 13 (4.2 g, 71% yield) as a clear colorless oil: [α]$^{23}_D$+6.6° (c 1.07, CHCl$_3$); IR (neat film) 2954(m), 1732 (s), 1713(s), 1416(m), 1250(m), 1057(s), 859(s), 835(s) cm$^{-1}$; $^1$H NMR (500 MHz, CDCl$_3$) δ9.69 (t, J=2.0 Hz, 1H), 4.56 (m, 2H), 3.53 (m, 2H), 3.40 (m, 1H), 3.31 (m, J=7.1 Hz, 1H), 3.26 (dd, J=7.5, 7.1 Hz, 1H), 1.00 (m, 5H), 0.86 (m, 2H), −0.05 (s, 9H); $^{13}$C NMR (125 MHz, CDCl$_3$) δ202.07, 94.86, 72.08, 65.08, 38.11, 29.00, 18.10, 17.08, −1.45; high resolution mass spectrum (CI, NH$_3$) m/z 250.1828 [(M+NH$_4$)]$^+$, calcd for C$_{11}$H$_{24}$O$_3$Si·NH$_4$ 250.1838.

Example 5

Monopyrrolinone (+)-15

To a solution of (−)-7 (2.0 g, 8.6 mmol) in toluene (60 mL) was added to (+)-6 (2.4 g, 8.6 mmol). The solution was stirred for 15 min; then the solution was concentrated in vacuo and the residue azeotropically dehydrated with additional toluene (5×60 mL). To a solution of the residue in THF (80 mL) was added 0.5 M KHMDS In toluene (43 mL, 21 mmol) rapidly via syringe. The resulting yellow-orange solution was stirred for 20 min and then 10% aqueous NaHSO$_4$ (100 mL) was added and diluted with EtOAc (100 mL). The resulting biphasic mixture was extracted with EtOAc (2×100 mL) and washed with saturated NaHCO$_3$ and brine (100 mL each). The resultant yellow solution was dried over MgSO$_4$ and concentrated in vacuo. The residue was purified by flash chromatography using methanol-dichloromethane (1:19) as the eluant to afford the monopyrrolinone (3.3 g, 93% yield) as a yellow oil: [a]$^{23}_D$+38.5° (c 1.07, CHCl$_3$); IR (CHCl$_3$) 3425(m), 3008(s), 2956(s), 2873 (s), 2836(m), 1710(m), 1661(s), 1583(s), 1465(s), 1422(s), 1368(s), 1250(s), 1121(s), 1057(s), 861(s), 837(s) cm$^{-1}$; $^1$H NMR (500 MHz, CDCl$_3$) δ7.77 (d, J=3.7 Hz, 1H), 5.61 (s, 1H), 4.65 (s, 2H), 4.47 (dd, J=4.1, 4.5 Hz, 1H), 3.61 (m, 3H), 3.42 (m, J=6.7 Hz, 1H), 3.35 (s, 3H), 3.28 (s, 3H), 2.81 (sx, J=6.7 Hz, 1H), 1.91 (dd, J=4.1 Hz, 1H), 1.66 (m, 2H), 1.52 (m, 2H), 1.16 (d, J=7.1 Hz 3H), 0.93 (m, 2H), 0.85 (d, J=6.3 Hz, 3H), 0.81 (d, J=6.7 Hz, 3H), 0.02 (s, 9H); $^{13}$C NMR (125 MHz, CDCl$_3$) δ203.80, 160.54, 115.81, 102.30, 94.96, 71.76, 67.99, 64392, 54.00, 53.14, 43.66, 40.29, 28.56, 24.33, 24.26, 24.13, 18.06, 16.85, −1.452; high resolution mass spectrum (ESI) m/z 438.2667 [(M+Na)]$^+$, calcd. for C$_{21}$H$_{41}$NO$_5$SiNa 438.2652.

Example 6

Monopyrrolinone Aldehyde

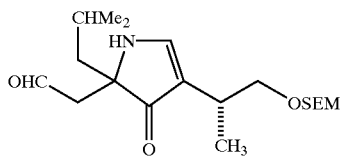

To a solution of (+)-15 (2.1 g, 5 mmol) in a 3:1 mixture of THF and water (70 mL) was added p-TsOH hydrate (943 mg, 5 mmol). The solution was heated at 50° C. for 4 h and was then cooled to room temperature and diluted with EtOAc (400 mL) and saturated NaHCO$_3$ (300 mL). The resulting biphasic mixture was extracted with EtOAc (2×200 mL) and washed with brine (200 mL). The yellow solution was then dried over MgSO$_4$ and concentrated in vacuo. The residue was purified by flash chromatography using methanol-dichloromethane (3:47) as the eluant to afford the monopyrrolinone aldehyde (1.82 g, 99% yield) as a yellow oil: [a]$^{23}_D$−43.8° (c 0.95, CHCl$_3$); IR (CHCl$_3$) 3447(m), 3008(s), 2957(s), 2928(s), 2873(s), 1722(s), 1661(s), 1582 (s), 1452(m), 1426(m), 1368(m), 1250(s), 1212(s), 1058(s), 1029(s), 861(s), 837(s) cm$^{-1}$; $^1$H NMR (500 MHz, CDCl$_3$) δ9.60 (d, J=2.6 Hz, 1H), 7.81 (d, J=3.7 Hz, 1H), 5.59 (s, 1H), 4.64 (s,2H), 3.61 (m, 3H), 3.45 (m, J=6.7 Hz, 1H), 2.81 (m, 1H), 2.76 (m, J=2.6 Hz, 1H), 2.56 (d, J=16.8 Hz, 1H). 1.73 (m, J=5.6 Hz, 1H), 1.66 (m, J=6.7 Hz, 1H), 1.58 (m, 1H), 1.16 (d, J=6.7 Hz, 3H), 0.93 (m, 2H), 0.88 (d,J=6.7 Hz, 3H), 0.81 (d, J=6.7 Hz, 3H), 0.02 (s, 9H); $^{13}$C NMR (125 MHz, CDCl$_3$) δ202.44,200.10, 160.51, 115.13. 94.88,71.45, 67.41, 64.92, 50.34, 44.42, 28.56, 24.26, 18.02, 16.82, −1.48; high resolution mass spectrum (ESI) m/z 392.2224 [(M+Na)]$^+$, calcd for C$_9$H$_{35}$NO$_4$SiNa 392.2233.

Example 7 bis-pyrrolinone (−)-16a

To a solution of (−)-14a (1.0 g, 4.5 mmol in toluene (60 mL) was added to (−)-monopyrrolinone aldehyde (1.8 g, 5 mmol). The solution was stirred for 15 min to allow formation of the imine after which the solution was concentrated in vacuo and the residue azeotropically dried with additional toluene (5×30 mL). To a solution of the residue in THF (40 ml) was added 0.5 M KHMDS in toluene (45 mL, 22 mmol) rapidly via syringe. The resulting yellow-orange solution was stirred for 45 min, and then 10% aqueous NaHSO$_4$ (100 mL) was added and diluted with EtOAc (100 mL). The resulting biphasic mixture was extracted with EtOAc (2×100 mL) and the combined organic phase was washed with saturated NaHCO$_3$ and brine (100 mL each). The yellow solution was dried over MgSO$_4$ and concentrated in vacuo. The residue was purified by flash chromatography using ethyl acetate as the eluant to afford the bis-pyrrolinone (2.3 g, 84% yield) as a yellow oil: [a]$^{23}_D$−97.2° (c 1.21, CHCl$_3$; IR (neat, film) 3272(s), 2953(s), 1708(s), 1643(s), 1556(s), 1468(s), 1248(s), 1188(s), 1122(s), 1057(s), 860(s), 836(s) cm$^{-1}$; $^1$H NMR (500 MHz, CDCl$_3$) δ8.22 (d, J=4.1 Hz, 1H), 7.80 (d, J=3.4 Hz, 1H), 7.03 (d, J=3.4 Hz, 1H), 5.99 (d, J=3.7 Hz, 1H), 4.65 (s, 2H), 4.48 (q, J=3.7, 4.1 Hz, 1H), 3.60 (m, 3H), 3.44 (d, J=7.1 Hz, 1H), 3.42 (d, J=7.4 Hz, 1H), 3.35 (s, 3H), 3.01 (s, 3H), 2.80 (m, 1H), 1.93 (dd, J=3.7, 4.1 Hz, 1H), 1.86 (m, J=4.1, 4.5 Hz, 1H), 1.72 (dd, J=7.5, 7.4 Hz, 1H), 1.61 (m, 2H), 1.38 (hp, J=6.7 Hz, 1H), 1.16 (m, 1H), 1.12 (d, J=7.1 Hz, 3H), 1.02 (d, J=6.7 Hz, 1H), 0.94 (m, 2H), 0.87 (d, J=6.3 Hz, 3H), 0.85 (d, J=6.3 Hz, 3H), 0.77 (d, J=6.7 Hz, 3H), 0.69 (d, J=6.3 Hz, 3H), 0.01 (s, 9H); $^{13}$C NMR (125 MHz, CDCl$_3$) δ203.02, 202.95, 161.48, 160.89, 114.82, 110.28, 102.00, 94.93, 71.80, 68.72, 67.78, 64.88, 53.91, 53.23,47.62, 43.72, 39.88, 28.45, 24.79, 24.47, 24.29, 24.05, 23.72, 18.06, 16.92, −1.44; high resolution mass spectrum (ESI) m/z 575.3475 [(M+Na)]$^+$, calcd for C$_{29}$H$_{52}$N$_2$O$_6$SiNa 575.3492.

Example 8 bis-CBZ Protected bis-pyrrolinone (+)-17c

To a solution of (−)-17a (2.1 g, 3.7 mmol) in THF (40 mL) at a −78° C. was added 1.0 M NaHMDS in THF (11 mL, 11 mmol) dropwise over 30 min. The resulting yellow solution was stirred for 5 min and then benzyl chloroformate (1.6 mL, 11 mmol) was added dropwise via syringe over 30 min. The yellow solution was stirred for 15 min at −78° C. and was warmed to room temperature. The solution was then poured into 10% aqueous $NaHSO_4$ (300 mL). The resulting biphasic mixture was extracted with EtOAc (2×200 mL) and the organic phase washed with saturated $NaHCO_3$ and brine (200 mL each), dried over $MgSO_4$ and concentrated in vacuo. The resulting yellow oil was purified by flash chromatography using EtOAc-hexanes (3:7) as the eluant to afford the bis-benzyloxycarbonyl-bis-pyrrolinone (2.5 g, 80%, yield) as a yellow oil: $[\alpha]^{23}_D$+47.90° (c 1.07, $CHCl_3$); IR (neat, film) 2955(m), 1698(s), 1614(s), 1402(s), 1278(s), 1057(s), 860(m), 836(m) $cm^{-1}$; $^1H$ NMR (500 MHz, $CDCl_3$) δ8.65 (br s), 8.41 (m), 8.25 (s), 8.35 (m), 5.24 (m), 4.60 (s), 4.08 (m), 3.57 (m), 3.50 (d, J=6.3 Hz), 3.48 {d, J=6.7 Hz), 3.23 (br s), 3.13 (br s), 3.04 (m), 2.81 (m), 2.43 (m), 2.11 (m), 1.84 (m), 1.55 (m), 1.42 (br s), 1.34 (br s), 1.17 (m), 0.90 (m), 0.79 (m), 0.70 {m), 0.57 (m), −0.01 (br s); $^{13}C$ NMR (125 MHz, $CDCl_3$) δ(complex spectrum due to rotomers); high resolution mass spectrum (ESI) m/z 843.4225 [(M+Na)]$^+$, calcd for $C_{45}H_{64}N_2O_{10}SiNa$ 843.4228.

Example 9

Alcohol (+)-18a

To a solution of (+)-17c (640 mg, 0.78 mmol) in a 1:1 mixture of THF and methanol (60 mL} was added p-TsOH (445 mg, 2.3 mmol). The solution was heated at 40° C. for 2.5 h and was then cooled to room temperature and diluted with $Et_2O$ and saturated $NaHCO_3$ (200 mL each). The resulting biphasic mixture was extracted with $Et_2O$ (2×100 mL) and washed with brine (100 mL). The yellow solution was then dried over $MgSO_4$ and concentrated in vacuo. The residue was purified by flash chromatography using EtOAc-hexanes (1:1) as the eluant to afford the bis-benzyloxycarbonyl-bis-pyrrolinone alcohol (500 mg, 93% yield) as a yellow oil: $[\alpha]^{23}_D$+22.0° (c 1.22, $CHCl_3$); IR ($CHCl_3$) 3520(b), 2956(m), 1722(m), 1693(m), 1682(m), 1606(m), 1402(m), 1203(m), 1148(m), 1062 (m) $cm^{-1}$; $^1H$ NMR (500 MHz, $CDCl_3$) δ9.13 (s), 8.44 (m), 8.24 (m), 7.35 (m), 5.27 (m), 5.06 (m), 4.07 (m), 3.93 (m), 3.73 (m), 3.52 (m), 3.44 (m), 3.18 (br 5), 3.11 (br s), 3.04 (br s), 2.96 (br s), 2.92 (br s), 2.67 (m), 2.50 (m), 2.16 (m}, 1.90 (m), 1.60 (m), 1.41 (m), 1.23 (m), 1.15 (d, J=7.1 Hz), 0.82 (m), 0.74 (m), 0.66 (m); $^{13}C$ NMR (125 MHz, $CDCl_3$) δ(complex spectrum due to rotomers}: high resolution mass spectrum (ESI) m/z 713.3416 [(M+Na)]$^+$, calcd for $C_{39}H_{50}N_2O_9Na$ 713.3414.

Example 10 bis-pyrrolinone Acid 18b

To a solution of (+)-18a (426 mg, 0.62 mmol) in dichloromethane (8 mL) was added the Dess-Martin periodinane (928 mg, 2.5 mmol). The heterogeneous mixture was stirred under air for 1.5 h. To the mixture was added saturated $NaHCO_3$ (30 mL), $Na_2S_2O_3$ (30 mL), and $Et_2O$ (40 mL). The mixture was stirred until the $Et_2O$ layer was clear (ca. 30 min). The resulting biphasic mixture was extracted with $Et_2O$ (3×40 mL) and the organic phase washed with saturated $NaHCO_3$ and brine (40 mL each), dried over $MgSO_4$ and concentrated in vacuo. To a solution of the above residue in t-BuOH (20 mL) was added 2-methyl-2-butene (1.21 mL, 2.4 mmol), premixed $NaClO_2$ (164 mg, 1.8 mmol) and $Na_2H_2PO_4$ (142 mg, 0.9 mmol) in water (4 mL). The solution was stirred for 2 h and then 10% aqueous $NaHSO_4$ (80 mL) and $Et_2O$ (80 mL) was added. The resulting biphasic mixture was extracted with $Et_2O$ (3×80 mL) and dried over $NaSO_4$ and concentrated in vacuo. The resulting clear oil was purified by flash chromatography using EtOAc-HOAc-hexanes (49:1:50) as the eluant to afford the bis-benzyloxycarbonyl-bis-pyrrolinone acid (350 mg, 81% yield, 2 steps) as a clear oil: $[\alpha]^{23}_D$+67.40° (c 2.78, $CHCl_3$); IR ($CHCl_3$) 2956(m), 1698(m), 1605(m), 1402(m), 1360 (m), 1200(m), 1147(m), 1091(m), 1058(m) $cm^{-1}$; $^1H$ NMR (500 MHz, $CDCl_3$) δ8.69 (brs), 8.58 (brs), 8.43 (brs), 7.35 (m), 5.27 (m), 5.14 (m), 4.09 (m), 3.54 (m), 3.23 (br s), 3.13 (br s), 3.04 (br s), 2.97 (br s), 2.46 (m), 2.23 (m), 2.09 (m), 1.87 (m), 1.56 (br s), 1.42 (m), 1.24 (m), 0.79 (m), 0.70 (br s), 0.59 (m); $^{13}C$ NMR (125 MHz, CDCl3) δ(complex spectrum due to rotomers); high resolution mass spectrum (ESI) m/z 727.3224 [(M+Na)]$^+$, calcd. for $C_{39}H_{48}N_2O_{10}Na$ 727.3207.

Example 11

Ester (+)-18c

To a solution of (+)-bis-pyrrolinone acid (64 mg, 0.1 mmol) in DMF (3 mL) was added diisopropylcarbodiimide (34 mg, 0.3 mmol), 1-hydroxybenzotriazol (37 mg, 0.3 mmol), and DMAP (ca. 1 mg). After 5 min, absolute ethanol (0.02 mL, 0.3 mmol) was added and the solution stirred for 7 h. The solution was diluted water and $Et_2O$ (40 mL each), separated, and the $Et_2O$ phase washed with brine (50 mL). The solution was dried over $MgSO_4$ and concentrated in vacuo. The residue was purified by flash chromatography using EtOAc-hexanes (4:6) as the eluant to afford the bis-benzyloxycarbonyl-bis-pyrrolinone ethyl ester (39 mg, 58% yield) as a light yellow oil: $[\alpha]^{23}_D$+89.9° (c 2.00, $CHCl_3$); IR ($CHCl_3$) 3019(m), 3012(m), 2961(m), 1726(s), 1608(m), 1404(s), 1224(s), 1060(s) $cm^{-1}$; $^1H$ NMR (500 MHz, $CDCl_3$) δ8.67 (br s), 8.54 (br s), 8.42 (br s), 7.38 (m), 5.26 (m), 4.12 (m, 4H), 4.07 (br s), 3.51 (q, J=7.1 Hz, 1H), 3.45 (m), 3.24 (br s), 3.14 (br s), 3.05 (br s), 2.98 (br s), 2.45 (m), 2.10 (m), 1.86 (m), 1.56 (m), 1.41 (m), 1.26 (br s), 1.21 (t, J=7.1 Hz), 0.80 (m), 0.72 (br s), 0.59 (m); $^{13}C$ NMR (125 MHz, $CDCl_3$) δ(complex spectrum due to rotomers); high resolution mass spectrum (ESI) m/z 755.3535 [(M+Na)]$^+$, calcd for $C_{41}H_{52}N_2O_{10}Na$ 755.3520.

Example 12

Acid (+)-19b

To a solution of (+)-18c (70 mg, 0.1 mmol) in wet THF (3 mL) was added p-TsOH (184 mg, 1 mmol). The solution was heated at 40° C. for 3 h and was then cooled to room temperature and diluted with $Et_2O$ (20 mL) and saturated $NaHCO_3$ (30 mL). The resulting biphasic mixture was extracted with $Et_2O$ (3×20 mL) and the combine $Et_2O$ phases washed with brine (20 mL). The solution was dried over $MgSO_4$ and concentrated in vacuo. To a solution of the above residue in t-BuOH (3.5 mL) was added 2-methyl-2-butene (0.19 mL, 0.38 mmol), premixed $NaClO_2$ (26 mg, 0.3 mmol) and $Na_2H_2PO_4$ (22 mg, 0.14 mmol) in water (0.7 mL). The solution was chilled to 0° C. and stirred for 1.5 h. To the mixture was added 10% aqueous $NaHSO_4$ (50 mL) and $Et_2O$ (50 mL). The resulting biphasic mixture was extracted with $Et_2O$ (3×40 mL), dried over $NaSO_4$ and concentrated in vacuo. The resulting clear oil was purified by flash chromatography using EtOAc-HOAc-hexanes (49:1:50) as the eluant to afford the bis-benzyloxycarbonylbis-pyrrolinone acid (40 mg, 59% yield for the 2 steps) as a light yellow oil: $[\alpha]^{23}_D$+68.2 (c 1.54, CHCl$_3$); IR (CHCl$_3$) 3019(m), 2962(w), 1727(s), 1609(w), 1405(s), 1212(s), 1091(w), 1061(w) cm$^{-1}$; $^1$H NMR (500 MHz, CDCl$_3$) δ8.46 (m), 7.36 (m), 5.22 (m), 4.12 (m,), 3.54 (m), 3.20 (br s), 2.74 (m), 2..49 (br s), 2.20 (m), 2.04 (m), 1.79 (brs), 1.58 {brs), 1.40 (m), 1.26 (brs), 1.21 (t, J=7.1 Hz), 0.78 (m), 0.71 {m), 0.69 {m), 0.63 (m); $^{13}$C NMR (125 MHz, CDCl$_3$) δ(complex spectrum due to rotomers); high resolution mass spectrum (ESI) m/z 725.3046 [(M+Na)]$^+$, calcd for $C_{39}H_{46}N_2O_{10}Na$ 725.3050.

Example 13 bis-benzyloxycarbonyl-bis-pyrrolinone 0-benzylhydroxyl amide 19c

To a solution of (+)-19b (25 mg, 0.04 mmol) in dichloromethane (2 mL) at 0° C. was added EDCl.HCl (10 mg, 0.054 mmol) and 1-hydroxybenzotriazole (7 mg, 0.054 mmol) and stirred for 30 min. The solution was warmed to room temperature for 1 h then cooled to 0° C. To the solution was added O-benzylhydroxylamine.HCl (17 mg, 0.108 mmol) and di-isopropylethyl-amine (0.04 mL, 0.252 mmol) and the resulting solution was stirred for 4 h. The solution was diluted with water and Et$_2$O (30 mL each) ant the Et$_2$O phase washed with saturated NaHCO$_3$ and brine (20 mL each), dried over MgSO$_4$ and concentrated in vacuo. The residue was purified by flash chromatography using methanol-dichloromethane (3:47) as the eluant to afford the bis-benzyloxycarbonyl-pyrrolinone O-benzylhydroxyl-amide (26 mg, 90% yield) as a light yellow oil: $[\alpha]^{23}_D$+72.6° (c 0.34, CHCl$_3$); IR (CHCl$_3$) 3018(w), 3010(w), 2962(w), 1726(s), 1607(w), 1404(s), 1210(s), 1091(w), 1061(w) cm$^{-1}$; $^1$H NMR (500 MHz, CDCl$_3$) δ8.41 (m, 3H), 7.34 (m), 5.28 (m), 5.08 (m), 4.81 (m), 4.12 (q, J=7.1 Hz, 2H), 3.52 (m, 1H), 2.86 (br s), 2.48 (br s), 2.16 (br s), 2.00 (brs), 1.88 (m), 1.59 (m), 1.39 (m), 1.26 (brs), 1.21 (t, J=7.1 Hz, 3H), 0.88 (m), 0.78 (m), 0.69 (m), 0.62 (m); $^{13}$C NMR (125 MHz, CDCl$_3$) δ(complex spectrum due to rotomers); high resolution mass spectrum (ESI) m/z 830.3664 [(M+Na)]$^+$, calcd for $C_{46}H_{53}N_3O_{10}Na$ 830.3629.

Example 14

Bispyrrolinone Hydroxamic Acid (−)-1a

To a solution of (+)-bis-benzyloxycarbonyl-bis-pyrrolinone O-benzylhydroxylamide (26 mg, 0.032 mmol) in ethanol (6 mL) was added 5% Pd/BaSO$_4$ (26 mg) and mixture was stirred under a hydrogen atmosphere (hydrogen filled balloon) for 17 h. The heterogeneous mixture was filtered through a 0.45 μm filter disc syringe ¼ filled with CELITE and then concentrated in vacuo. The resulting residue was purified by flash chromatography using isopropyl alcohol-hexanes (3:7) as the eluant to afford the hydroxamic acid (8 mg, 57% yield) as a light yellow film: $[\alpha]^{23}$D− 172.5° (c 0.80, CHCl$_3$); IR (CHCl$_3$) 3243(w), 3021(w),2959 (w), 2929 (w), 2872(w), 1724(w), 1650(m), 1576(m), 1446 (w), 1174(w) cm$^{-1}$; $^1$H NMR (500 MHz, CDCl$_3$) δ(concentration dependent spectrum) 10.10 (s br, 1H), 8.31 (s, 1H), 8.01 (d, J=3.7 Hz, 1H), 7.51 (s, 1H), 7.27 (s, 1H), 4.12 (q, J=6.9, 7.4 Hz, 2H), 3.49 (q, J=6.9, 7.4 Hz, 1H), 2.54 (d, J=13.9 hz, 1H), 2.29 (d, J=14.3 Hz, 1H), 1.94 (m, 1H), 1.63 (m, 5H), 1.40 (s,1H), 1.32 (d, J=7.4 Hz, 3H), 1.23 (t, J=6.9 Hz, 3H), 0.86 (d, J=6.0 Hz, 3H), 0.81 (d, J=6.5 Hz, 3H), 0.78 (d, J=6.5 Hz, 3H), 0.66 (d, J=6.5 Hz, 3H); $^{13}$C NMR (125 MHz, CDCl$_3$) δ202.39, 201.62, 174.95, 167.01, 162.57, 162.04, 111.49, 108.98, 68.93, 68.09, 60.71, 46.45, 43.51, 40.45, 33.79, 24.58, 24.49, 24.29, 24.15, 23.78, 23.48, 17.44, 14.14; high resolution mass spectrum (ESI) m/z 472.2432 [(M+Na)]$^+$ calcd. for $C_{23}H_{35}N_3O_6Na$ 472.2424.

Example 15 bis-pyrrolinone carboxylic acid (−)-19d

To a solution of (+)-19b (11 mg, 0.016 mmol) in ethanol (3 mL) was added 5% Pd/BaSO$_4$ (10 mg) and the mixture stirred under a hydrogen atmosphere (hydrogen filled balloon) for 2 h. The heterogeneous mixture was filtered through a 0.45 μm filter disc syringe ¼ filled with CELITE and concentrated in vacuo. The resulting residue was purified by flash chromatography using acetic acid-methanol-dichloromethane (1:10:90) as the eluant to afford the bis-pyrrolinone carboxylic acid (4 mg. 58% yield) as a light yellow film: $[\alpha]^{23}_D$−235.1° (c 0.70 CHCl$_3$); IR (CHCl$_3$) 3436(m), 3026(m), 3018(m), 2958(s), 2932(s), 2872(m), 1723(s), 1648(s), 1576(s), 1448(s), 1368(m), 1168(s) cm$^{-1}$; $^1$H NMR (500 MHz, CDCl$_3$) δ(concentration dependent spectrum) 8.30 (d, J=3.3 Hz, 1H), 7.98 (d, J=2.9 Hz, 1H), 7.12 (s, 1H), 6.72 (s, 1H), 4.12 (q, J=7.5, 7.0 Hz, 2H), 3.50 (q, J=7.1 Hz, 1H), 2.69 (d, J=16.4 Hz, 1H). 2.41 (d, J=16.8 Hz, 1H), 1.95 (m, 1H), 1.82 (dd, J=14.1, 4.8 Hz, 1H), 1.63 (m, 4H), 1.42 (m, 1H), 1.31 (d, J=7.1 Hz, 3H), 1.23 (t, J=7.1 Hz, 3H), 0.87 (d, J=6.3 Hz, 3H), 0.82 (d, J=6.3 Hz, 3H), 0.80 (d, J=6.7 Hz, 3H), 0.67 (d, J=6.7 Hz, 3H); $^{13}$C NMR (125 MHz, CDCl$_3$) δ202.48, 201.62, 174.84, 173.38, 162.04, 161.69, 111.68, 108.89, 68.12, 67.96, 60.72, 46.67, 43.31, 41.23, 33.68, 24.62, 24.42, 24.27, 24.23, 23.79, 23.38, 17.53, 14.14; high resolution mass spectrum (ESI) m/z 457.2317 [(M+Na)]$^+$, calcd. for $C_{23}H_{34}N_2O_6Na$ 457.2315.

Thus, while there have been described what are presently believed to be the preferred embodiments of the invention, those skilled in the art will realize that other and further embodiments can be made without departing from the spirit of the invention, and thus it is intended to include all such further modifications and changes come within the true scope of the claims as set forth herein.

We claim:
1. A compound having formula (1):

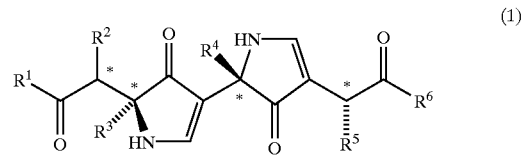

wherein:
R$^1$ is —NHOH or —OH;
R$^2$ is hydrogen, C$_{1-6}$ alkyl;
R$^3$ and R$^4$ are selected independently from a group consisting of the side chains of the naturally occurring α-amino acids, C$_{1-6}$ alkyl, (CH$_2$)$_n$Ar wherein the aryl group is optionally substituted with up to two groups independently selected from the group consisting of phenyl, hydroxy, C$_{1-4}$ alkoxy, phenoxy, —O(CH$_2$)$_m$OH, C$_{1-4}$ thioalkyl, halogens, nitro, cyano, C$_{1-4}$ alkylsulfonyl, and C$_{1-4}$ alkylsulfinyl wherein m is 1 or 2 and n is 0 to 3;
R$^5$ is hydrogen, C$_{1-6}$ alkyl;
R$^6$ is OR$^7$, NR$^7$R$^8$ wherein R$^7$ and R$^8$ taken independently are selected from a group consisting of hydrogen, C$_{1-4}$ alkyl, C$_{1-4}$ branched alkyl, alkyl aryl and benzyl; and, a stereoisomer, enantiomer, diastereomer, hydrate or pharmaceutically acceptable salt thereof.

2. A compound according to claim 1 wherein:

$R^1$ is —NHOH or —OH;

$R^2$ is H or $CH_3$;

$R^3$ is n-$C_{1-6}$ alkyl, s-$C_4H_9$, i-$C_4H_9$, $(CH_2)_n$Ar, $(CH_2)_n$-p-$C_6H_4$OMe, $(CH_2)_n$-p-$C_6H_4$—$C_6H_5$ or $(CH_2)_n$-p-$C_6H_4$O$C_6H_5$ and n is 0 to 2;

$R^4$ is hydrogen, Me, i-$C_4H_9$ or n-$C_4H_9$;

$R^5$ is hydrogen or Me;

$R^6$ is $OR^7$ or $NR^7R^8$ wherein $R^7$ and $R^8$ are selected independently from the group consisting of hydrogen, Me, Et or $CH_2$Ph.

3. A compound according to claim 1 wherein:

$R^1$ is —NHOH or —OH;

$R^2$ is H or $CH_3$;

$R^3$ and $R^4$ are selected independently from the group consisting of the side chains of naturally occurring α-amino acids;

$R^5$ is hydrogen, $C_{1-6}$ alkyl;

$R^6$ is $OR^7$ or $NR^7R^8$ wherein $R^7$ and $R^8$ are selected independently from the group consisting of hydrogen, Me, Et or $CH_2$Ph.

4. A compound according to claim 1 wherein:

$R^1$ is —NHOH or —OH;

$R^2$ is H or $CH_3$;

$R^3$ and $R^4$ are selected independently from the group consisting of the side chains of naturally occurring hydrophobic α-amino acids;

$R^5$ is hydrogen, $C_{1-6}$ alkyl;

$R^6$ is $OR^7$ or $NR^7R^8$ wherein $R^7$ and $R^8$ are selected independently from the group consisting of hydrogen, Me, Et or $CH_2$Ph.

5. A compound according to claim 1 wherein:

$R^1$ is NHOH;

$R^2$ is H;

$R^3$ and $R^4$ are i-$C_3H_7$; i-$C_4H_9$, s-$C_4H_5$, $CH_2C_6H_5$, $CH_2C_6H_4$-p-OMe, (3-indolinyl)methyl;

$R^5$ is hydrogen, $CH_3$;

$R^6$ is $OR^7$;

$R^7$ is OMe or OEt.

6. A method of inhibiting pathological changes mediated by elevated levels of matrix metalloproteases in mammals comprising administration to a mammal in need thereof a therapeutically effective amount of a matrix metalloprotease inhibiting compound according to claim 1.

7. A method of treating an inflammatory disorder comprising administration to a mammal in need thereof a therapeutically effective amount of a matrix metalloprotease inhibiting compound according to claim 1.

8. A method according to claim 6 wherein the condition treated is osteoarthritis, rheumatoid arthritis, septic arthritis, periodontal disease, gingivitis, solid tumor growth and tumor invasion by secondary metastasis, corneal ulceration, dermal ulceration, epidermolysis bullosa, neural degeneration, multiple sclerosis and surgical wound healing.

9. A pharmaceutically composition comprising a pharmaceutical carrier and a therapeutically effective amount of a matrix metalloprotease inhibiting compound according to claim 1.

* * * * *

UNITED STATES PATENT AND TRADEMARK OFFICE
CERTIFICATE OF CORRECTION

PATENT NO. : 6,455,570 B1
DATED : September 24, 2002
INVENTOR(S) : Smith, III et al.

It is certified that error appears in the above-identified patent and that said Letters Patent is hereby corrected as shown below:

Column 20,
Line 12, after "is", replace "OMe or OEt" with -- Me or Et --.

Signed and Sealed this

Second Day of September, 2003

JAMES E. ROGAN
*Director of the United States Patent and Trademark Office*